(12) United States Patent
Nieminen (10) Patent No.: US 11,647,977 B2
(45) Date of Patent: May 16, 2023

(54) DEVICE INCLUDING ULTRASOUND, AUSCULTATION, AND AMBIENT NOISE SENSORS

(71) Applicant: EchoNous, Inc., Redmond, WA (US)

(72) Inventor: Greg Nieminen, Bothell, WA (US)

(73) Assignee: EchoNous, Inc., Redmond, WA (US)

( * ) Notice: Subject to any disclaimer, the term of this patent is extended or adjusted under 35 U.S.C. 154(b) by 766 days.

(21) Appl. No.: 16/593,173

(22) Filed: Oct. 4, 2019

(65) Prior Publication Data

US 2020/0107800 A1 Apr. 9, 2020

Related U.S. Application Data

(60) Provisional application No. 62/742,714, filed on Oct. 8, 2018.

(51) Int. Cl.
*A61B 7/02* (2006.01)
*A61B 7/04* (2006.01)
(Continued)

(52) U.S. Cl.
CPC .............. *A61B 7/026* (2013.01); *A61B 5/332* (2021.01); *A61B 5/7203* (2013.01); *A61B 7/04* (2013.01);
(Continued)

(58) Field of Classification Search
CPC ....... A61B 7/04; A61B 8/4444; A61B 5/7203; A61B 7/026; A61B 5/332;
(Continued)

(56) References Cited

U.S. PATENT DOCUMENTS

| 3,954,098 A | 5/1976 | Dick et al. |
| 4,100,916 A | 7/1978 | King |

(Continued)

FOREIGN PATENT DOCUMENTS

| EP | 3 191 062 B1 | 3/2021 |
| JP | 10-127626 A | 5/1998 |

(Continued)

OTHER PUBLICATIONS

Ramireddy et al., "Ultrasound Probe with Integrated ECG lead: Feasibility Study," Ultrasonic Imaging, 29, 195-198, 2007.

(Continued)

*Primary Examiner* — Oommen Jacob
(74) *Attorney, Agent, or Firm* — Seed Intellectual Property Law Group LLP (57) ABSTRACT

Devices and methods in which auscultation signals, ultrasound signals, and ambient noise signals may be simultaneously acquired by a same handheld device are provided. Moreover, in some embodiments, electrocardiogram (EKG) may be acquired by the handheld device. One such device includes a housing having a sensor portion at a distal end of the housing, and a handle portion between a proximal end and the distal end of the housing. An ultrasound sensor is positioned at least partially within the sensor portion of the housing, and a first auscultation sensor is positioned at least partially within the sensor portion of the housing. An ambient noise sensor is positioned at least partially within the housing between the handle portion and the proximal end of the housing.

18 Claims, 5 Drawing Sheets

(51) Int. Cl.
- *A61B 8/00* (2006.01)
- *A61B 5/00* (2006.01)
- *A61B 5/332* (2021.01)
- *G01S 15/02* (2006.01)
- *B06B 1/06* (2006.01)
- *B06B 1/02* (2006.01)

(52) U.S. Cl.
CPC .......... *A61B 8/4444* (2013.01); *A61B 8/4488* (2013.01); *A61B 2560/0247* (2013.01); *B06B 1/0292* (2013.01); *B06B 1/0607* (2013.01); *G01S 15/02* (2013.01)

(58) Field of Classification Search
CPC ........ A61B 2560/0247; A61B 5/02438; A61B 5/0245; A61B 8/0883; A61B 8/4455; A61B 8/0891; A61B 8/06; A61B 8/4416; A61B 5/318; A61B 8/5207; B06B 1/0292; B06B 1/0607; G01S 15/02; G01S 7/52079; G01S 15/8915; G10K 11/175
See application file for complete search history.

(56) References Cited

U.S. PATENT DOCUMENTS

| | | | |
|---|---|---|---|
| 4,154,230 A | 5/1979 | Lee | |
| 4,304,240 A | 12/1981 | Perlin | |
| 4,515,164 A | 5/1985 | Slavin | |
| 4,572,202 A | 2/1986 | Thomenius | |
| 4,592,236 A | 6/1986 | Battagin et al. | |
| 4,651,716 A | 3/1987 | Forester et al. | |
| 5,159,931 A | 11/1992 | Pini | |
| 5,178,149 A | 1/1993 | Imburgia et al. | |
| 5,295,486 A | 3/1994 | Wollschläger et al. | |
| 5,360,005 A | 11/1994 | Wilk | |
| 5,398,691 A | 3/1995 | Martin et al. | |
| 5,539,831 A * | 7/1996 | Harley | G10K 11/17881 381/151 |
| 5,690,111 A | 11/1997 | Tsujino | |
| 5,749,833 A | 5/1998 | Hakki et al. | |
| 5,812,678 A * | 9/1998 | Scalise | A61B 7/003 381/71.7 |
| 5,960,089 A | 9/1999 | Bouricius et al. | |
| 6,139,500 A | 10/2000 | Clark | |
| 6,152,884 A | 11/2000 | Bjorgaas | |
| 6,213,944 B1 | 4/2001 | Miller et al. | |
| 6,454,716 B1 | 9/2002 | Zumeris | |
| 6,514,201 B1 | 2/2003 | Greenberg | |
| 6,547,730 B1 | 4/2003 | Lin et al. | |
| 6,624,551 B2 | 9/2003 | Orten | |
| 6,626,831 B2 | 9/2003 | Holley et al. | |
| 6,673,017 B1 | 1/2004 | Jackson | |
| 7,211,045 B2 | 5/2007 | Dala-Krish et al. | |
| 7,247,139 B2 | 7/2007 | Yudkovitch et al. | |
| 7,300,406 B2 | 11/2007 | Carter | |
| 7,303,530 B2 | 12/2007 | Barnes et al. | |
| 7,393,326 B2 * | 7/2008 | Bindefeld | A61B 8/4472 600/453 |
| 7,450,746 B2 | 11/2008 | Yang et al. | |
| 7,539,532 B2 | 5/2009 | Tran | |
| 7,686,766 B2 | 3/2010 | Quistgaard et al. | |
| 7,697,982 B2 | 4/2010 | Brodnick | |
| 7,713,208 B2 | 5/2010 | Kamiyama | |
| 7,792,314 B2 | 9/2010 | Ramakrishnan et al. | |
| 7,862,511 B2 | 1/2011 | Rafter | |
| 7,981,038 B2 | 7/2011 | Kanade et al. | |
| 7,987,303 B2 | 7/2011 | Bartlett | |
| 8,057,390 B2 | 11/2011 | Witte et al. | |
| 8,092,396 B2 | 1/2012 | Bagha et al. | |
| 8,226,562 B2 | 7/2012 | Pelissier et al. | |
| 8,241,217 B2 | 8/2012 | Chiang et al. | |
| D675,738 S | 2/2013 | Baumer et al. | |
| 8,388,538 B2 | 3/2013 | Younge et al. | |
| 8,591,417 B2 | 11/2013 | Suzuki et al. | |
| 8,622,910 B2 | 1/2014 | Kuban et al. | |
| 8,680,991 B2 | 3/2014 | Tran | |
| 8,764,660 B2 | 7/2014 | Frigstad et al. | |
| 8,778,699 B2 | 7/2014 | Yerramilli et al. | |
| 9,069,063 B2 | 6/2015 | Schreckenberg et al. | |
| 9,078,571 B2 | 7/2015 | Bridger et al. | |
| 9,089,278 B2 | 7/2015 | Saigo et al. | |
| 9,161,721 B2 | 10/2015 | Yang | |
| 9,192,352 B2 | 11/2015 | Yao et al. | |
| 9,192,360 B2 | 11/2015 | Na et al. | |
| 9,220,440 B2 | 12/2015 | Addison et al. | |
| 9,237,881 B2 | 1/2016 | Chono et al. | |
| 9,259,160 B2 | 2/2016 | Watson et al. | |
| 9,301,032 B1 * | 3/2016 | Bello | A61B 5/02438 |
| 9,326,753 B2 | 5/2016 | Nishimura | |
| 9,345,452 B2 | 5/2016 | Miyake | |
| 9,349,098 B1 | 5/2016 | Lonson | |
| 9,366,754 B2 | 6/2016 | Buckton et al. | |
| 9,414,786 B1 | 8/2016 | Brockway et al. | |
| 9,451,896 B2 | 9/2016 | Bauer | |
| 9,545,228 B2 | 1/2017 | Bardy et al. | |
| 9,561,015 B2 | 2/2017 | Halmann et al. | |
| 9,662,504 B2 | 5/2017 | Dong et al. | |
| 9,717,412 B2 | 8/2017 | Roham et al. | |
| 9,746,448 B2 | 8/2017 | Gu | |
| 9,901,252 B2 | 2/2018 | Tran | |
| 9,907,535 B2 | 3/2018 | Barthe et al. | |
| 10,874,377 B2 * | 12/2020 | Pagoulatos | A61B 5/14551 |
| 2004/0225476 A1 | 11/2004 | Tien | |
| 2004/0236223 A1 * | 11/2004 | Barnes | A61B 8/4254 600/459 |
| 2005/0165310 A1 | 7/2005 | Bindefeld | |
| 2006/0004290 A1 | 1/2006 | Smith et al. | |
| 2007/0186325 A1 | 8/2007 | Torrent Lopez et al. | |
| 2008/0071184 A1 | 3/2008 | Carter | |
| 2008/0281206 A1 * | 11/2008 | Bartlett | A61B 8/56 600/459 |
| 2009/0099446 A1 * | 4/2009 | Frigstad | A61B 8/14 600/437 |
| 2009/0312638 A1 | 12/2009 | Bartlett | |
| 2010/0286527 A1 | 11/2010 | Cannon et al. | |
| 2010/0331708 A1 | 12/2010 | Hatib | |
| 2011/0213272 A1 * | 9/2011 | Telfort | A61B 7/003 600/586 |
| 2011/0245651 A1 | 10/2011 | Nakamura | |
| 2011/0275909 A1 | 11/2011 | Kim | |
| 2012/0065479 A1 | 3/2012 | Lahiji et al. | |
| 2013/0053657 A1 | 2/2013 | Ziamo et al. | |
| 2013/0123646 A1 | 5/2013 | Choi | |
| 2013/0158363 A1 * | 6/2013 | Zoghbi | A61B 5/0013 600/301 |
| 2013/0345563 A1 | 12/2013 | Stuebe et al. | |
| 2014/0323865 A1 * | 10/2014 | Hoppmann | A61B 8/4416 600/443 |
| 2014/0336690 A1 | 11/2014 | Zhadkevich | |
| 2014/0371574 A1 | 12/2014 | Shusterman et al. | |
| 2015/0065814 A1 | 3/2015 | Kapoor | |
| 2015/0065881 A1 | 3/2015 | Cho et al. | |
| 2015/0086954 A1 | 3/2015 | Hoppmann et al. | |
| 2015/0119758 A1 * | 4/2015 | Rogers | A61B 5/7203 600/586 |
| 2015/0223782 A1 | 8/2015 | Yamagata et al. | |
| 2015/0293214 A1 | 10/2015 | Cannon et al. | |
| 2015/0294085 A1 | 10/2015 | Kare et al. | |
| 2015/0327775 A1 | 11/2015 | Carter | |
| 2016/0045183 A1 | 2/2016 | Lee et al. | |
| 2016/0066797 A1 | 3/2016 | Lee et al. | |
| 2016/0100817 A1 * | 4/2016 | Hussain | A61B 7/04 600/528 |
| 2016/0287207 A1 * | 10/2016 | Xue | A61B 7/04 |
| 2016/0296200 A1 | 10/2016 | Hinojosa | |
| 2016/0338590 A1 | 11/2016 | Sagalovich et al. | |
| 2016/0374571 A1 | 12/2016 | Narayan et al. | |
| 2017/0014079 A1 | 1/2017 | Lee et al. | |
| 2017/0086778 A1 | 3/2017 | Cahan et al. | |
| 2017/0112439 A1 | 4/2017 | Dubin et al. | |
| 2017/0164930 A1 | 6/2017 | Oh et al. | |
| 2017/0231508 A1 | 8/2017 | Edwards et al. | |

(56) References Cited

U.S. PATENT DOCUMENTS

| | | |
|---|---|---|
| 2017/0252004 A1 | 9/2017 | Broad et al. |
| 2017/0262982 A1 | 9/2017 | Pagoulatos et al. |
| 2018/0000405 A1 | 1/2018 | Penders et al. |
| 2018/0049716 A1 | 2/2018 | Rajagopal et al. |
| 2018/0070913 A1 | 3/2018 | Sahin |

FOREIGN PATENT DOCUMENTS

| | | | |
|---|---|---|---|
| RU | 2 539 990 C2 | 1/2015 | |
| RU | 2015 152 075 A | 6/2017 | |
| WO | 2005/013819 | 2/2005 | |
| WO | 2005/037096 | 4/2005 | |
| WO | WO-2005037096 A1 * | 4/2005 | ............... A61B 8/04 |
| WO | 2006/082286 | 8/2006 | |
| WO | 2008/120154 A2 | 10/2008 | |
| WO | 2012/158652 A2 | 11/2012 | |
| WO | 2016/078992 | 5/2016 | |
| WO | 2016/207092 | 12/2016 | |

OTHER PUBLICATIONS

U.S. Appl. No. 16/715,956, filed Dec. 16, 2019, System and Method for Fusing Ultrasound with Additional Signals.

Chinese Search Report for CN Application No. 2018800649579, dated May 10, 2022, 2 pages.

Russian Search Report for RU Application No. 2020114954/14(024839), dated Feb. 25, 2022, 2 pages.

First Examination Report for Indian Application No. 202117020271, dated Dec. 14, 2022, 6 pages.

* cited by examiner

DEVICE INCLUDING ULTRASOUND, AUSCULTATION, AND AMBIENT NOISE SENSORS

BACKGROUND

Technical Field

The present application pertains to physiological sensing devices, systems and methods, and more particularly to such devices, systems and methods for acquiring ultrasound, electrocardiography, and auscultation data.

Description of the Related Art

Ultrasound imaging is typically performed in a clinical setting, by trained ultrasound experts, utilizing ultrasound systems that are specifically designed to acquire ultrasound data. Similarly, electrocardiography (EKG) is typically performed in a clinical setting by trained experts and utilizing equipment that is specifically designed for acquiring electrocardiography data. Auscultation data is typically acquired by a physician or other clinician utilizing a stethoscope.

Acquisition of these different types of clinical data, i.e., ultrasound data, EKG data, and auscultation data, is thus conventionally performed utilizing separate pieces of equipment, and often in separate patient visits or separate environments.

The signals acquired by a stethoscope may include ambient noise that is sensed by the stethoscope, in addition to the target sounds (e.g., the auscultation signals) that are sensed by the stethoscope. Such ambient noise may vary depending on a variety of factors, such as the environment in which the stethoscope is used, and may include noises generated by other electronic equipment in the environment, noises generated by the user's hand, or the like.

BRIEF SUMMARY

The present disclosure provides devices and methods in which ambient noise detected by an ambient noise sensor can be canceled from auscultation sounds detected by one or more auscultation sensors. The devices may include an ultrasound sensor and an EKG sensor, in addition to the ambient noise sensor and the auscultation sensors. Such devices may simultaneously acquire ultrasound, electrocardiography, and auscultation signals, which in some embodiments, may be synchronized with one another.

In an embodiment, a device is provided that includes a housing having a sensor portion at a distal end of the housing, and a handle portion between a proximal end and the distal end of the housing. An ultrasound sensor is positioned at least partially within the sensor portion of the housing, and a first auscultation sensor is positioned at least partially within the sensor portion of the housing. An ambient noise sensor is positioned at least partially within the housing between the handle portion and the proximal end of the housing.

In another embodiment, an ultrasound probe is provided that includes an ultrasound sensor, an electrocardiogram (EKG) sensor, a first auscultation sensor, an ambient noise sensor, and a processor. The processor is communicatively coupled to the auscultation sensor and the ambient noise sensor. In use, the processor receives an auscultation signal sensed by the first auscultation sensor and an ambient noise signal sensed by the ambient noise sensor, and generates a noise-canceled auscultation signal in which the ambient noise signal is canceled from the auscultation signal.

In yet another embodiment, the present disclosure provides a method that includes: detecting ultrasound signals by an ultrasound sensor positioned adjacent to a sensing surface of a handheld device; detecting auscultation signals by at least one auscultation sensor positioned adjacent to the sensing surface of the handheld device; detecting ambient noise signals by an ambient noise sensor positioned between a handle portion of the handheld device and a proximal end of the handheld device, the ambient noise sensor being spaced apart from the sensor surface by at least the handle portion; and generating a noise-canceled auscultation signal by canceling the ambient noise signal from the auscultation signal.

DETAILED DESCRIPTION

Three primary techniques used extensively in medicine for physiological assessment, e.g., of the cardiothoracic cavity, include sonography, auscultation, and electrocardiography. Each technique provides different kinds of information usable to assess the anatomy and physiology of the organs present in a region of interest, e.g., the cardiothoracic cavity.

Medical ultrasound imaging (sonography) has been one of the most effective methods for examining both the heart and the lungs. Ultrasound imaging provides anatomical information of the heart as well as qualitative and quantitative information on blood flow through valves and main arteries such as the aorta and pulmonary artery. One significant advantage of ultrasound imaging is that, with its high frame rate, it can provide dynamic anatomical and blood flow information which is vital for assessing the condition of the heart which is always in motion. Combined with providing blood flow information, ultrasound imaging provides one of the best available tools for assessing the structure and function of heart chambers, valves, and arteries/veins. Similarly, ultrasound imaging can assess fluid status in the body and is the best tool in assessing pericardial effusion (fluid around the heart).

In the case of lungs, ultrasound imaging provides information on the anatomical structure of the lungs with the ability to show specific imaging patterns associated with various lung diseases and with an ability to assess fluid status around the lung and within individual compartments of the lung including the assessment of pericardial effusion.

Auscultation allows for assessing the physiological condition and function of organs such as the heart and lungs by capturing audible sounds that are produced by or otherwise associated with these organs. The condition and function of these organs, or other organs as the case may be, can be evaluated based on clinical information indicating how different sounds are associated with various physiological phenomena and how the sounds change for each pathological condition.

Electrocardiography (EKG or ECG) is focused on the heart by capturing the electrical activity of the heart as it is related to the various phases of the cardiac cycle. The condition and function of the heart may be evaluated based on clinical knowledge indicating how the electrical activity of the heart changes based on various pathological conditions.

The present disclosure provides devices and methods in which auscultation, EKG, and ultrasound signals may be acquired by a single handheld device. Moreover, the handheld device may acquire ambient noise signals by an ambient noise sensor that is spaced apart from the auscultation, EKG, and ultrasound sensors. The ambient noise may be canceled or subtracted from the auscultation signals, thereby producing a clear auscultation signal which is more useful, for example, to a physician or user of the handheld device.

Figure 1:
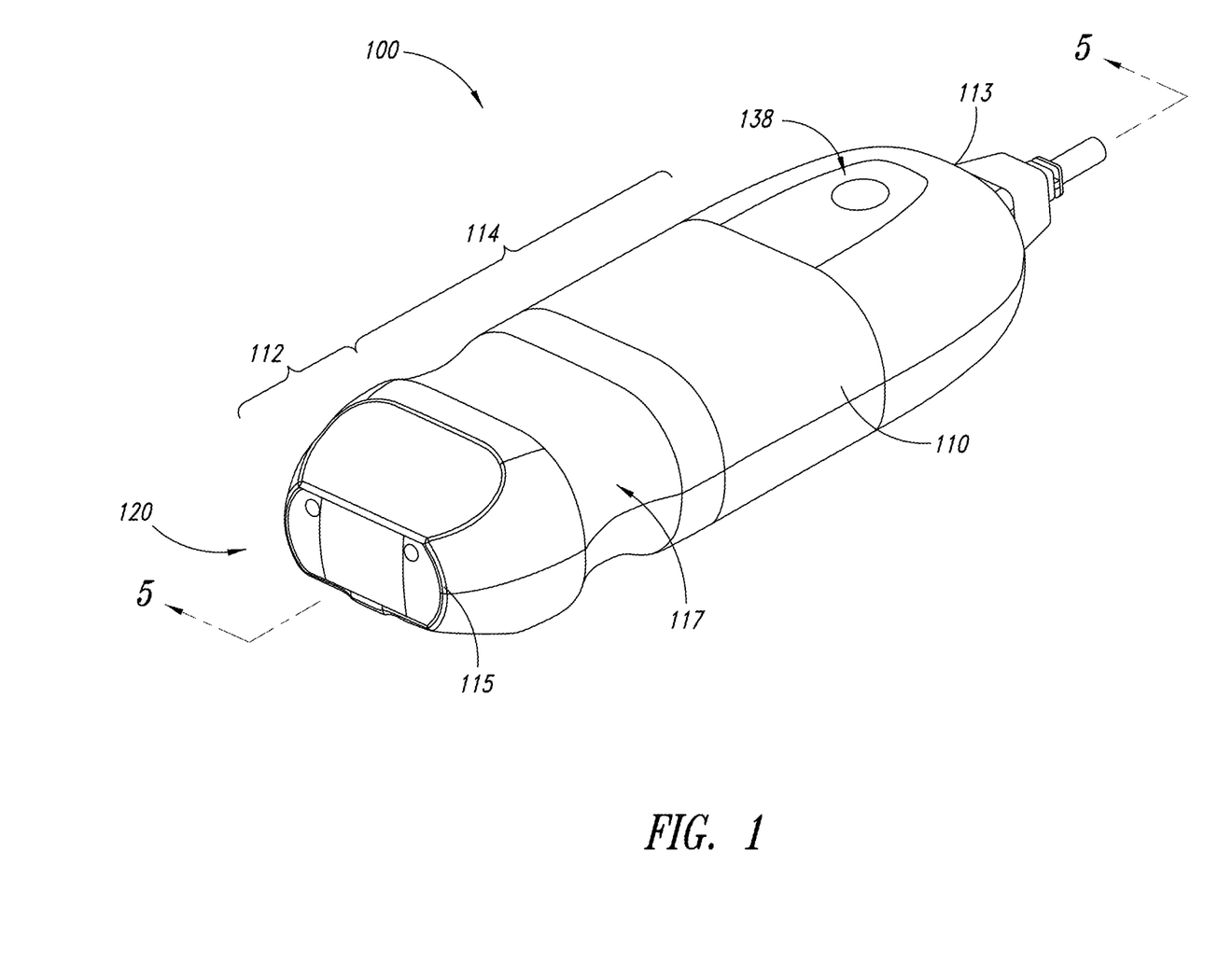
FIG. 1 is a perspective view illustrating a device having an ultrasound sensor, an auscultation sensor, and an ambient noise sensor, in accordance with one or more embodiments of the present disclosure.

FIG. 1 is a perspective view illustrating a device 100, which is operable to acquire ultrasound, electrocardiographic, and auscultation signals, in accordance with embodiments of the present disclosure.

The device 100 includes a housing 110, which forms an external portion of the device 100. The housing 110 includes a sensor portion 112 near a distal end 115 of the housing 110, and a handle portion 114 between a proximal end 113 and the distal end 115 of the housing 110. The handle portion 114 is proximally located with respect to the sensor portion 112.

The handle portion 114 is a portion of the housing 110 that is gripped by a user to hold, control, and manipulate the device 100 during use. The handle portion 114 may include gripping features, such as one or more detents 117, and in some embodiments, the handle portion 114 may have a same general shape as portions of the housing 110 that are distal to, or proximal to, the handle portion 114. In general, the handle portion 114 refers to a portion of the housing 110 that is located between the sensor portion 112 and an ambient noise sensor 138, which will be described in further detail later herein.

The housing 110 surrounds internal electronic components and/or circuitry of the device 100, including, for example, electronics such as driving circuitry, processing circuitry, oscillators, beamforming circuitry, filtering circuitry, and the like. The housing 110 may be formed to surround or at least partially surround externally located portions of the device 100, such as a sensor face 120, and may a sealed housing, such that moisture, liquid or other fluids are prevented from entering the housing 110. The housing 110 may be formed of any suitable materials, and in some embodiments, the housing 110 is formed of a plastic material. The housing 110 may be formed of a single piece (e.g., a single material that is molded surrounding the internal components) or may be formed of two or more pieces (e.g., upper and lower halves) which are bonded or otherwise attached to one another.

Figure 2:
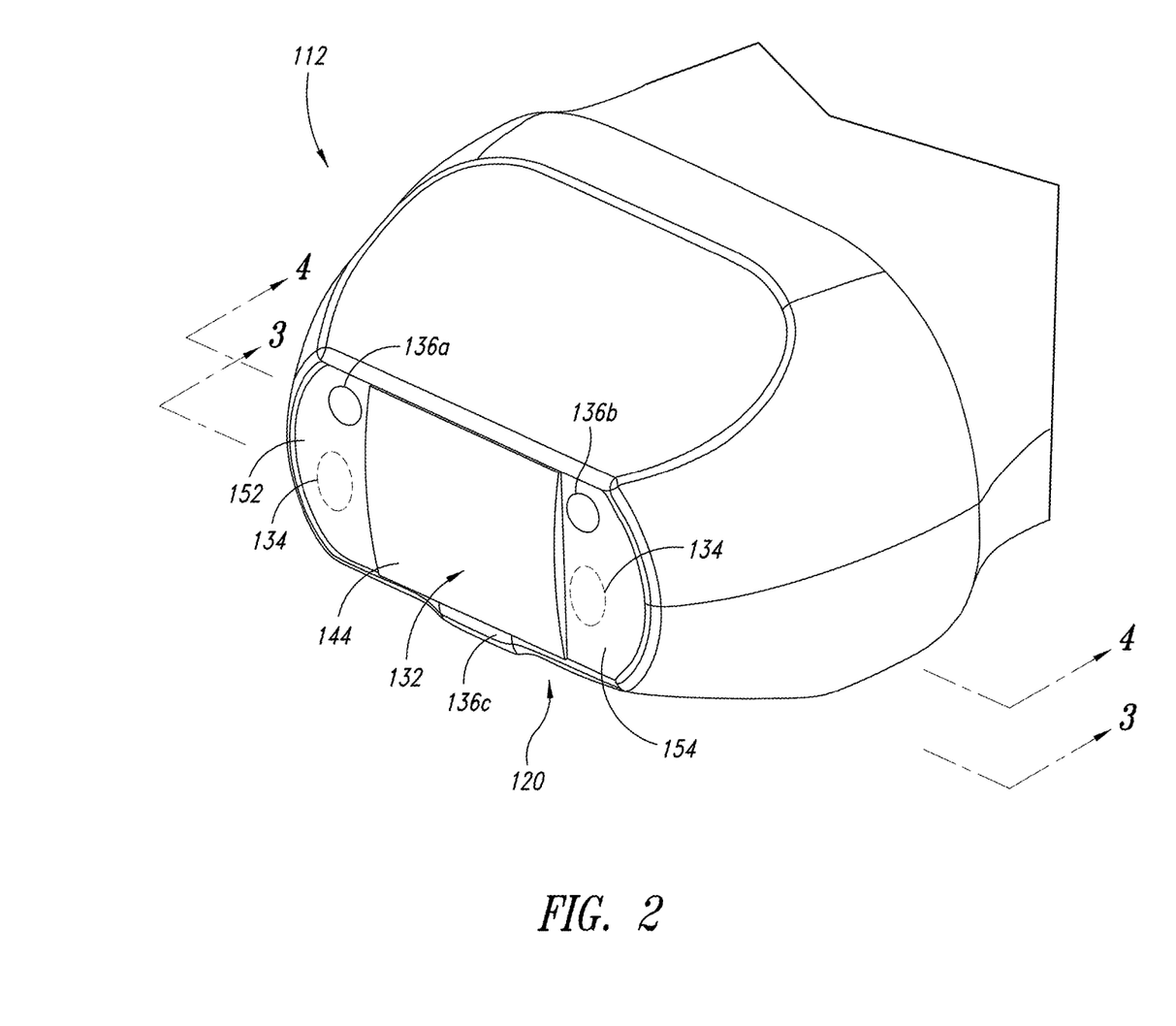
FIG. 2 is an enlarged perspective view of a sensor portion of the device shown in FIG. 1, in accordance with one or more embodiments.

FIG. 2 is an enlarged perspective view of the sensor portion of the device shown in FIG. 1. As shown in further detail in FIG. 2, the sensor portion 112 of the device 100 includes an ultrasound sensor 132, and at least one auscultation sensor 134. In some embodiments, the sensor portion 112 includes an electrocardiogram (EKG) sensor 136, which may include a plurality of EKG leads or electrodes 136a, 136b, 136c. Each of the ultrasound sensor 132, the at least one auscultation sensor 134, and the EKG sensor 136 are positioned adjacent to the sensor face 120 of the device 100. In use, the sensor face 120 may be placed in contact with a patient's skin, and the device 100 may obtain ultrasound, auscultation, and EKG signals via the ultrasound sensor 132, the at least one auscultation sensor 134, and the EKG sensor 136, respectively.

As shown in FIGS. 1 and 2, in some embodiments, the device 100 includes two auscultation sensors 134 adjacent to the sensor face 120. The auscultation sensors 134 may be any sensor operable to detect internal body sounds of a patient, including, for example, body sounds associated with the circulatory, respiratory, and gastrointestinal systems. For example, the auscultation sensors 134 may be microphones. In some embodiments, the auscultation sensors 134 may be electronic or digital stethoscopes, and may include or otherwise be electrically coupled to amplification and signal processing circuitry for amplifying and processing sensed signals, as may be known in the relevant field.

Referring again to FIG. 1, the device 100 further includes an ambient noise sensor 138 positioned at least partially within the housing between the handle portion 114 and the proximal end 113 of the housing 110. The ambient noise sensor 138 may be any microphone suitable to detect ambient sounds. The ambient noise sensor 138 senses ambient sounds, and a noise-canceled signal may be generated in which the ambient sounds are canceled from the target sounds (e.g., heart sounds of a patient) that are sensed by the auscultation sensors 134.

The ambient sounds that are sensed by the ambient noise sensor 138 may be, for example, sounds generated by electronic equipment, sounds generated by the ultrasound sensor 132 (e.g., by an ultrasound array), sounds generated by a user of the device 100, such as by movement of the user's hands, or any other sounds that may be present in an environment in which the device 100 is used.

The ultrasound sensor 132 includes an ultrasound array or transducer 142 (FIG. 3) configured to transmit an ultrasound signal toward a target structure in a region of interest in the patient. The transducer 142 is further configured to receive echo signals returning from the target structure in response to transmission of the ultrasound signal. To that end, the transducer 142 may include transducer elements that are capable of transmitting an ultrasound signal and receiving subsequent echo signals. In various embodiments, the transducer elements may be arranged as elements of a phased array. Suitable phased array transducers are known in the art.

Figure 3:
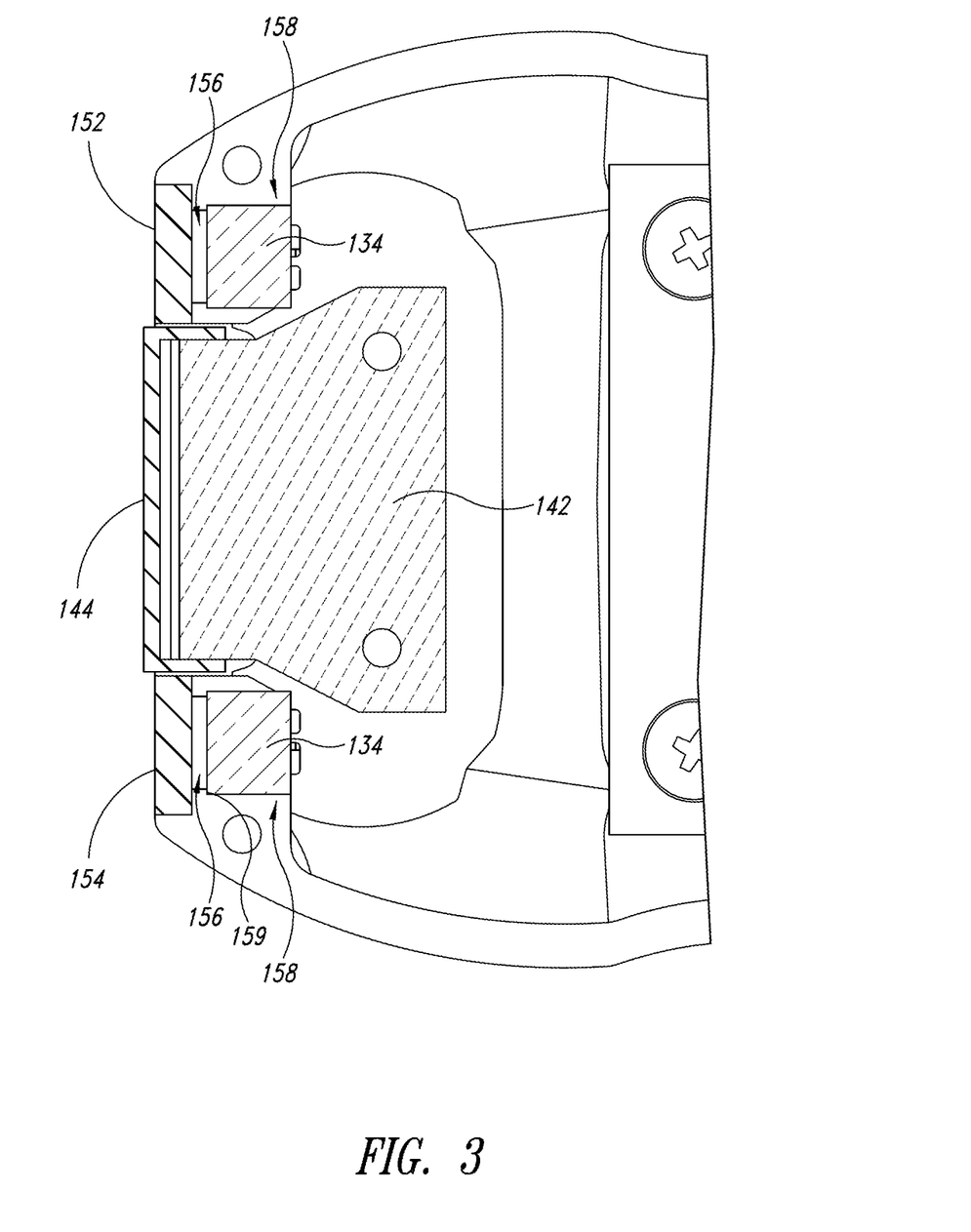
FIG. 3 is a cross-sectional view taken along the cut-line 3-3 of FIG. 2, illustrating further details of the sensing portion of the device, in accordance with one or more embodiments.

The transducer 142 of the ultrasound sensor 132 may be a one-dimensional (1D) array or a two-dimensional (2D) array of transducer elements. The transducer array may include piezoelectric ceramics, such as lead zirconate titanate (PZT), or may be based on microelectromechanical systems (MEMS). For example, in various embodiments, the ultrasound sensor 132 may include piezoelectric micromachined ultrasonic transducers (PMUT), which are microelectromechanical systems (MEMS)-based piezoelectric ultrasonic transducers, or the ultrasound sensor 132 may include capacitive micromachined ultrasound transducers (CMUT) in which the energy transduction is provided due to a change in capacitance.

The ultrasound sensor 132 may further include an ultrasound focusing lens 144, which is positioned distally with respect to the ultrasound transducer 142, and which may form a part of the sensor face 120. The focusing lens 144 may be any lens operable to focus a transmitted ultrasound beam from the ultrasound transducer 142 toward a patient and/or to focus a reflected ultrasound beam from the patient to the transducer 142. The ultrasound focusing lens 144 may have a curved surface shape in some embodiments. The ultrasound focusing lens 144 may have different shapes, depending on a desired application, e.g., a desired operating frequency, or the like. The ultrasound focusing lens 144 may be formed of any suitable material, and in some embodiments, the ultrasound focusing lens 144 is formed of a room-temperature-vulcanizing (RTV) rubber material.

The EKG sensor 136 may be any sensor that detects electrical activity, e.g., of a patient's heart, as may be known in the relevant field. For example, the EKG sensor 136 may include any number of electrodes 136a, 136b, 136c, which in operation are placed in contact with a patient's skin and are used to detect electrical changes in the patient that are due to the heart muscle's pattern of depolarizing and repolarizing during each heartbeat.

As shown in FIG. 2, the EKG sensor 136 may include a first electrode 136a that is positioned adjacent to a first side of the ultrasound sensor 132 (e.g., adjacent to the left side of the ultrasound focusing lens 144, as shown), and a second electrode 136b that is positioned adjacent to a second side of the ultrasound sensor 132 that is opposite to the first side (e.g., adjacent to the right side of the ultrasound focusing lens 144, as shown). The EKG sensor 136 may further include a third electrode 136c that is positioned adjacent to a third side of the ultrasound sensor 132 (e.g., adjacent to the lower side of the ultrasound focusing lens 144, as shown). In some embodiments, each of the first, second, and third electrodes 136a, 136b, 136c have different polarities. For example, the first electrode 136a may be a positive (+) electrode, the second electrode 136b may be a negative (−) electrode, and the third electrode 136c may be a ground electrode.

The number and positions of the EKG sensor electrodes may vary in different embodiments. As shown in FIG. 2, the electrodes 136a, 136b, 136c may be approximately equidistant from one another. The first and second electrodes 136a, 136b may be positioned near a top edge of the distal end 115 of the housing 110, while the third electrode 136c may be positioned between the lower side of the ultrasound sensor 132 and a bottom edge of the distal end 115 of the housing 110.

In some embodiments, first and second membranes 152, 154 are positioned adjacent to opposite sides of the ultrasound sensor 132 and may form a part of the sensor face 120. The membranes 152, 154 may be formed of any suitable material, and in some embodiments, the membranes 152, 154 are formed of a room-temperature-vulcanizing (RTV) rubber material. In some embodiments, the membranes 152, 154 are formed of a same material as the ultrasound focusing lens 144.

In some embodiments, the sensor face 120 includes a sealant which seals the sensor face 120 of the device 100 so that it is compliant with ingress protection specifications of IPX7 of the IP Code (as published by the International Electrotechnical Commission) (e.g., it is liquid tight when submerged to a depth of at least one meter). The sealant may be provided, for example, between the membranes 152, 154 and the respective sides of the ultrasound sensor 132, and/or between the ultrasound sensor 132, the membranes 152, 154 and the side surfaces of the distal end 115 of the housing 110. In some embodiments, the sealant is provided over the ultrasound focusing lens 144 of the ultrasound sensor 132 and the membranes 152, 154. The sealant may be a RTV rubber material, and in some embodiments, the sealant may be formed of a same material as the ultrasound focusing lens 144 and/or the membranes 152, 154.

As shown in FIG. 3, the membranes 152, 154 are positioned in front of (i.e., distally with respect to) the auscultation sensors 134. In some embodiments, the auscultation sensors 134 are spaced apart from the membranes 152, 154 by respective gaps 156, which may be air gaps.

The auscultation sensors 134 may be positioned in respective auscultation sensor sockets 158, which may fix a position of the auscultation sensors 134 so that they are spaced apart from the respective membranes 152, 154 by a desired gap 156. In some embodiments, the auscultation sensor sockets 158 are formed as an internal piece of the housing 110. For example, the auscultation sensor sockets 158 may be molded into the housing 110. The auscultation sensor sockets 158 may be sized to accommodate the auscultation sensors 134, and the auscultation sensors 134 may be securely held in the auscultation sensor sockets 158. In some embodiments, the auscultation sensors 134 may be secured within the auscultation sensor sockets 158 by an adhesive material.

The auscultation sensor sockets 158 may include distal flanges 159 which impede movement of the auscultation sensors 134 in the distal direction. That is, the distal flanges 159 may have a dimension that is smaller than a perimeter dimension of the auscultation sensors 134, so that the auscultation sensors 134 cannot fit through the distal flanges 159. Instead, the auscultation sensors 134 may be fixed in a position (e.g., in abutting contact) by the distal flanges 159 of the auscultation sensor sockets 158. The distal flanges 159 may have a thickness which defines the distance of the gaps 156. That is, the distal flanges 159 may extend between surfaces of the auscultation sensors 134 and respective surfaces of the first and second membranes 152, 154, and the openings within the distal flanges 159 may define the distance of gaps 156. In some embodiments, the gaps 156 has a distance within a range of about 0.5 mm to about 1.5 mm, inclusive. In some embodiments, the gaps 156 have a distance of about 1 mm.

With the auscultation sensors 134 positioned in the auscultation sensor sockets 158 and spaced apart from the membranes 152, 154 by a desired gap 156, the membranes 152, 154 may operate as diaphragms which convert mechanical vibrations (e.g., from motion against the membranes 152, 154 and/or in response to receiving acoustic vibrations) into sounds which are detectable by the auscultation sensors 134.

Figure 4:
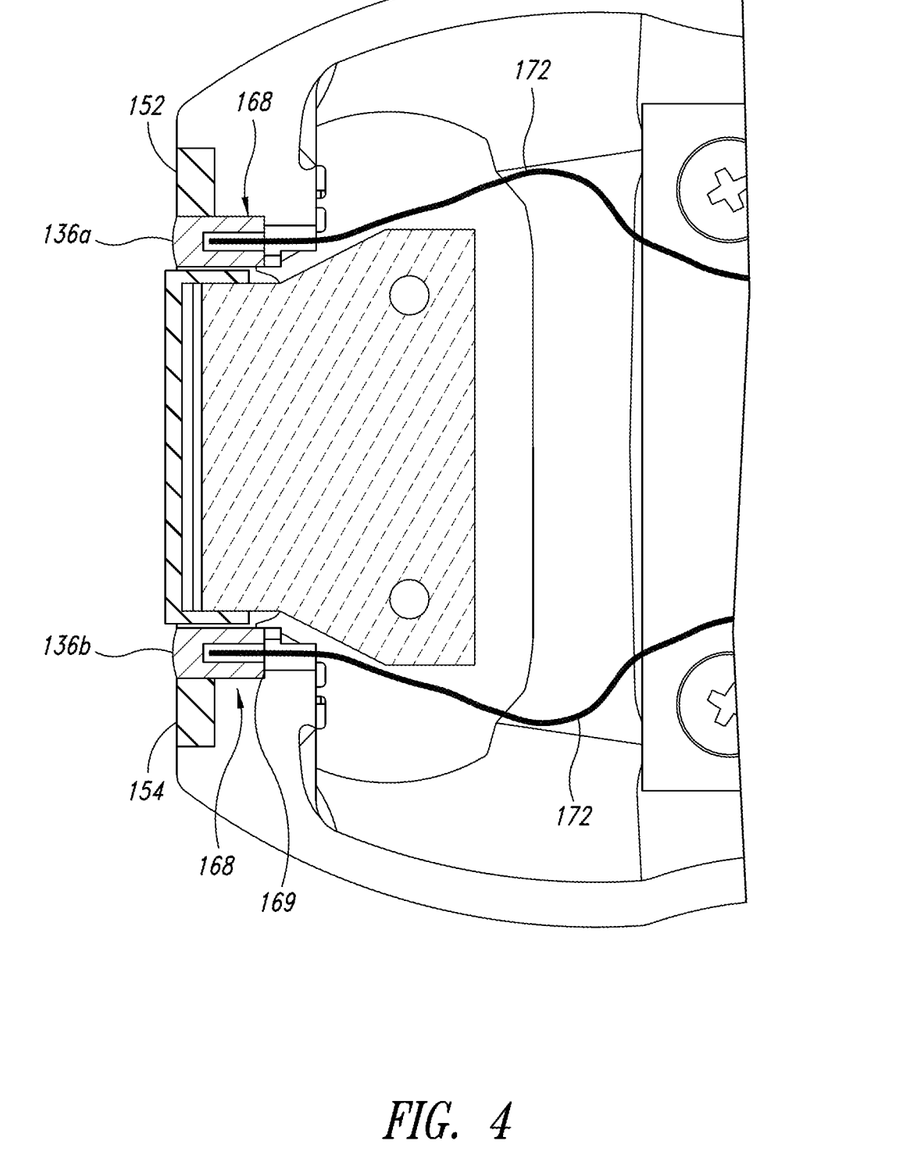
FIG. 4 is a cross-sectional view taken along the cut-line 4-4 of FIG. 2, illustrating further details of the sensing portion of the device, in accordance with one or more embodiments.

FIG. 4 is a cross-sectional view taken along the cut-line 4-4 of FIG. 2, illustrating further details of the sensing portion of the device, in accordance with one or more embodiments. In particular, FIG. 4 illustrates further details of the first and second EKG sensor electrodes 136a, 136b.

As shown in FIG. 4, the first and second electrodes 136a, 136b may be positioned in respective EKG electrode sockets 168, which may hold the electrodes 136a, 136b in a desired position. In some embodiments, the EKG electrode sockets 168 are formed as an internal piece of the housing 110, and may be molded into the housing 110. The EKG electrode sockets 168 may be sized to accommodate the electrodes 136a, 136b, and the electrodes 136a, 136b may be securely held in the EKG electrode sockets 168. In some embodiments, the electrodes 136a, 136b may be secured within the EKG electrode sockets 168 by an adhesive material.

While the cross-section illustration of FIG. 4 shows only the first and second electrodes 136a, 136b and corresponding EKG electrode sockets 168, the third electrode 136c may be held in a desired position along the sensor face 120 by a same or similar EKG electrode socket 168 that is sized to accommodate the third electrode 136c.

The EKG electrode sockets 168 may include proximal flanges 169 which impede movement of the electrodes 136a, 136b in the proximal direction. That is, the proximal flanges 169 may have a dimension that is smaller than a perimeter dimension of the electrodes 136a, 136b, so that the electrodes 136a, 136b cannot fit through the proximal flanges 169.

The electrodes 136a, 136b may extend through the membranes 152, 154 so that the electrodes 136a, 136b are exposed along the sensor face 120. For example, the first electrode 136a may extend through the first membrane 152, and the second electrode 136b may extend through the second membrane 154. Similarly, the third electrode 136c may be exposed along the sensor face 120.

The membranes 152, 154 may have openings through which the electrodes 136a, 136b may extend, and the membranes 152, 154 may contact side surfaces of the electrodes 136a, 136b so that the electrodes 136a, 136b are substantially sealed along the sensor face 120. In some embodiments, a sealant, which may be a RTV rubber material, may be provided between the membranes 152, 154 and the electrodes 136a, 136b and the sealant may be formed of a same material as the ultrasound focusing lens 144 and/or the membranes 152, 154.

EKG leads or wires 172 are attached to the electrodes 136a, 136b, 136c and may electrically couple the electrodes 136a, 136b, 136c to processing circuitry.

Figure 5:
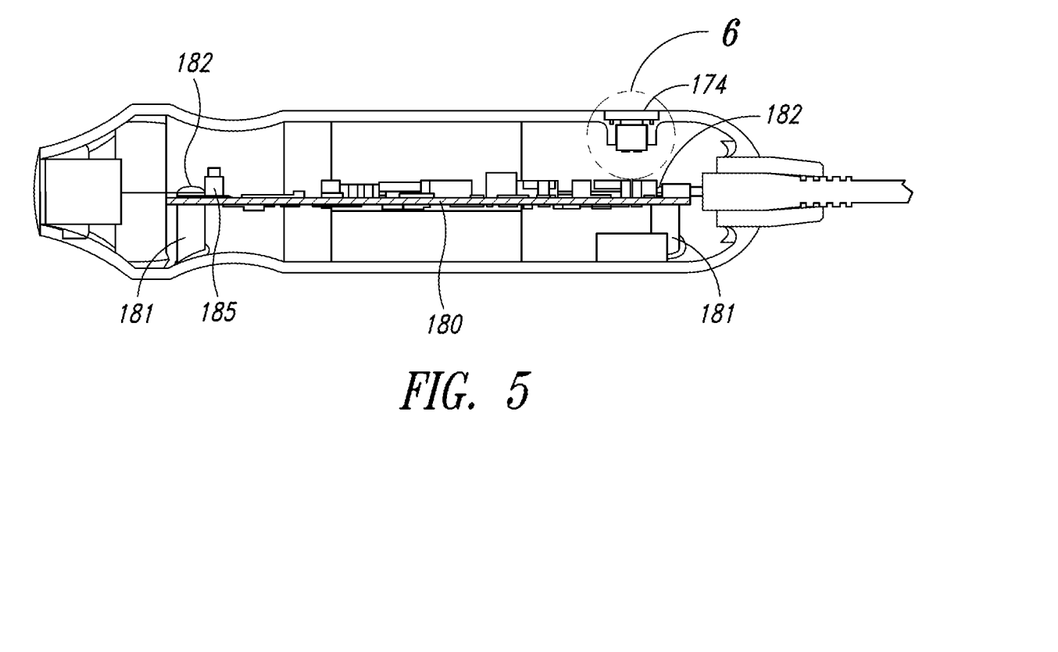
FIG. 5 is a cross-sectional view taken along the cut-line 5-5 of FIG. 1, illustrating further details of the device, in accordance with one or more embodiments.
Figure 6:
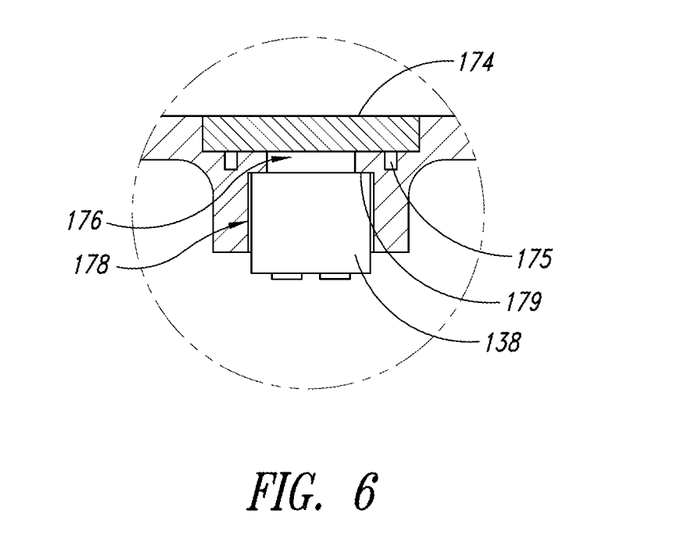
FIG. 6 is an enlarged cross-sectional view showing further details of an ambient noise sensor of the device, in accordance with one or more embodiments.

FIG. 5 is a cross-sectional view taken along the cut-line 5-5 of FIG. 1, illustrating further details of the device 100, in accordance with one or more embodiments. FIG. 6 is an enlarged cross-sectional view of a region 6 of FIG. 5, showing further details of an ambient noise sensor of the device 100 in accordance with one or more embodiments.

Referring now to FIGS. 5 and 6, the device 100 may include an internal board 180, and various circuitry and components may be attached to the board 180. The internal board 180 may be any structure suitable to hold or carry the various circuitry and components included within the housing 110. In some embodiments, the internal board 180 is a printed circuit board (PCB) and may include wires, conductive traces, conductive vias, or the like for electrically coupling one or more circuits or components of the device 100 to each other. The internal board 180 may be coupled to the housing 110 by any suitable technique. In some embodiments, one or more threaded receptacles 181 are attached to or otherwise formed as part of the housing 110, and the internal board 180 may be coupled to the housing 110 by one or more threaded fasteners 182, such as screws, which are threaded into the threaded receptacles 181.

The ambient noise sensor 138 may be positioned in an ambient noise sensor socket 178, which may fix a position of the ambient noise sensor 138. The ambient noise sensor socket 178 may be substantially similar to the auscultation sensor sockets 158 shown in FIG. 3, except that the ambient noise sensor socket 178 may be oriented in a direction (e.g., vertical direction as shown) that is transverse to the direction in which the auscultation sensor sockets are oriented (e.g., horizontal direction). An ambient noise sensor membrane 174 is positioned over the ambient noise sensor 138 and may form an external portion of the device 100. That is, the ambient noise sensor membrane 174 may be exposed to the external environment.

The ambient noise sensor membrane 174 may be formed of any suitable material, and in some embodiments, the ambient noise sensor membrane 174 is formed of a room-temperature-vulcanizing (RTV) rubber material. In some embodiments, the ambient noise sensor membrane 174 may be formed of a same material as the first and second membranes 152, 154 and/or the ultrasound focusing lens 144. The ambient noise sensor membrane 174 may have any shape, and in some embodiments, the ambient noise sensor membrane 174 has a substantially circular shape in top plan view. In some embodiments, the ambient noise sensor membrane 174 may have a diameter of about 10 mm, and may have a thickness of about 2 mm.

The ambient noise sensor 138 may be positioned in the ambient noise sensor socket 178, which may fix a position of the ambient noise sensor 138 so that it is spaced apart from the ambient noise sensor membrane 174 by a desired gap 176, which may be an air gap. In some embodiments, the ambient noise sensor socket 178 is formed as an internal piece of the housing 110, for example, the ambient noise sensor socket 178 may be molded into the housing 110. In some embodiments, the ambient noise sensor 138 may be secured within the ambient noise sensor socket 178 by an adhesive material, such as glue or any other adhesive.

One or more slots or grooves 175 may be included in the housing 110 and positioned adjacent to the ambient noise sensor socket 178. The grooves 175 are configured to accommodate excess adhesive materials which may be used to attach the ambient noise sensor 138 to the ambient noise sensor socket 178.

The ambient noise sensor socket 178 may include a flange 179 which impedes movement of the ambient noise sensor 138 and fixes a position of the ambient noise sensor 138 with respect to the ambient noise sensor socket 178. The flange 179 may be substantially similar to the distal flanges 159 of the auscultation sensor sockets 158, and may have a thickness which defines the distance of the gap 176. In some embodiments, the gap 176 between the ambient noise sensor 138 and the ambient noise sensor membrane 174 has a distance within a range of about 0.5 mm to about 1.5 mm, inclusive. In some embodiments, the gap 176 has a distance of about 1 mm. In some embodiments, the gap 176 has a distance that is substantially the same as a distance of the gaps 156 between the auscultation sensors 134 and the membranes 152, 154.

In some embodiments, the ambient noise sensor socket 178 and/or the ambient noise sensor membrane 174 may be omitted. For example, in some embodiments, the ambient noise sensor 138 may be mounted at any suitable position within the housing 110, including rigidly mounted on the inside of the housing 110. Alternatively or additionally, the ambient noise sensor 138 may be mounted without the ambient noise sensor membrane 174. In some embodiments, the ambient noise sensor 138 may be mounted directly on the internal board 180, which may be a PCB as previously described herein.

As shown in FIG. 5, the device 100 may include a variety of different electrical components, circuitry, and the like. For example, the device 100 may include processing circuitry 185 which may communicatively coupled (e.g., by one or more wires, by a wireless communication path, or the like) to the auscultation sensors 134 and to the ambient noise sensor 138. In some embodiments, the processing circuitry 185 may be implemented at least in part as software that is loadable or executable by one or more hardware structures, such as a microcontroller, microprocessor, or the like.

The processing circuitry 185 is configured to receive an auscultation signal sensed by the auscultation sensors 134 and an ambient noise signal sensed by the ambient noise sensor 138, and generate a noise-canceled auscultation signal in which the ambient noise signal is canceled from the auscultation signal. The processing circuitry 185 may generate the noise-canceled auscultation signal by any suitable techniques. In some embodiments, the processing circuitry 185 may generate a cancellation waveform that is a negative of the ambient noise signal sensed by the ambient noise sensor 138, and may mix the cancellation waveform with the auscultation signal sensed by the auscultation sensors 134 in order to produce the noise-canceled auscultation signal.

The processing circuitry 185 may further include or otherwise be coupled to audio processing circuitry for processing the signals received from the auscultation sensors 134 and the ambient noise sensor 138, including, for example, filters, amplifiers, preconditioning and digitization circuitry, and the like. The device 100 may further include EKG signal processing circuitry, ultrasound processing and/or driving circuitry or any other circuitry that may be utilized during operation of the device 100 and which may facilitate operations of the device 100 as described herein. Such processing and/or driving circuitry may be positioned on the internal board 180 and may be coupled to the processing circuitry 185. In some embodiments, such processing and/or driving circuitry may be included at least partially in the processing circuitry 185.

The device 100 may further include one or more computer-readable memories, which may be any computer-readable storage medium, including, for example, read-only memory (ROM), random access memory (RAM), flash memory, hard disk drive, optical storage device, magnetic storage device, electrically erasable programmable read-only memory (EEPROM), organic storage media, or the like. The computer-readable memory may be coupled to the processing circuitry 185, and in some embodiments the memory may store the various signals acquired by the device 100. The signals may be stored in the memory in a synchronized manner, or with associated information for synchronizing the signals.

In operation, a user may place the sensor face 120 of the device 100 in a desired location on a patient's body. Once suitably positioned, the device 100 receives signals from the auscultation sensors 134, the EKG sensor 136, and the ultrasound sensor 132 at the sensor face 120. At the same time, device 100 receives ambient noise signals from the ambient noise sensor 138, and generates a noise-canceled auscultation signal based on the auscultation signals received from the auscultation sensors 134 and the ambient noise signals received from the ambient noise sensor 138.

In some embodiments, the signals acquired from one or more of the auscultation sensors 134, the EKG sensor 136, the ultrasound sensor 132, and the ambient noise sensor 138 may be simultaneously acquired and synchronized with one another. For example, U.S. patent application Ser. No. 15/969,632, assigned to the assignee of the present disclosure and incorporated by reference herein in its entirety, describes various embodiments of devices, systems, and methods in which auscultation data, EKG data, and ultrasound data, which are derived from signals received by an auscultation sensor, an EKG sensor, and an ultrasound sensor, respectively, are synchronized.

The signal acquisition and synchronization techniques described in U.S. patent application Ser. No. 15/969,632 may be modified and implemented in embodiments of the present disclosure for similarly synchronizing the acquired auscultation, EKG, and ultrasound signals, as well as the acquired ambient noise signals.

The various embodiments described above can be combined to provide further embodiments. All of the U.S. patent applications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
    a housing having a sensor portion at a distal end of the housing, and a handle portion between a proximal end and the distal end of the housing;
    an ultrasound sensor positioned at least partially within the sensor portion of the housing;
    a first auscultation sensor positioned at least partially within the sensor portion of the housing, wherein the sensor portion of the housing includes a first auscultation sensor socket, the first auscultation sensor being positioned in the first auscultation sensor socket;
    an ambient noise sensor positioned at least partially within the housing between the handle portion and the proximal end of the housing;
    an electrocardiogram (EKG) sensor positioned at least partially within the sensor portion of the housing, the EKG sensor including a first electrode adjacent to a first side of the ultrasound sensor, a second electrode adjacent to a second side of the ultrasound sensor that is opposite the first side, and a third electrode adjacent to a third side of the ultrasound sensor;
    a second auscultation sensor, wherein the sensor portion of the housing includes a second auscultation sensor socket, the second auscultation sensor being positioned in the second auscultation sensor socket, and wherein the first and second auscultation sensor sockets are positioned adjacent to the first and second sides of the ultrasound sensor, respectively;
    a first membrane adjacent to the first side of the ultrasound sensor, the first auscultation sensor positioned between the first membrane and the proximal end of the housing; and
    a second membrane adjacent to the second side of the ultrasound sensor, the second auscultation sensor positioned between the second membrane and the proximal end of the housing.

2. The device of claim 1 wherein the first electrode of the EKG sensor extends through the first membrane, and the second electrode of the EKG sensor extends through the second membrane.

3. The device of claim 1 wherein the ambient noise sensor is mounted to the housing in a direction that is transverse to a direction in which the first and second auscultation sensor sockets are oriented.

4. The device of claim 1 wherein the first auscultation sensor is spaced apart from the first membrane by a first gap, and the second auscultation sensor is spaced apart from the second membrane by a second gap.

5. The device of claim 4 wherein each of the first gap and the second gap is within a range of about 0.5 mm to about 1.5 mm, inclusive.

6. The device of claim 3 wherein the housing includes a third membrane over the ambient noise sensor.

7. The device of claim 1 wherein the ultrasound sensor includes an ultrasound transducer array and an ultrasound focusing lens, the ultrasound transducer array being positioned between the ultrasound focusing lens and the proximal end of the housing.

8. The device of claim 7 wherein the ultrasound transducer array, the first membrane, and the second membrane are formed of a same material.

9. The device of claim 8 wherein the ultrasound transducer array, the first membrane, and the second membrane are formed of a room-temperature-vulcanizing (RTV) rubber material.

10. The device of claim 1, further comprising:
processing circuitry communicatively coupled to the first auscultation sensor and the ambient noise sensor,
wherein the processing circuitry, in use, receives an auscultation signal sensed by the first auscultation sensor and/or the second auscultation sensor and an ambient noise signal sensed by the ambient noise sensor, and generates a noise-canceled auscultation signal in which the ambient noise signal is canceled from the auscultation signal.

11. An ultrasound probe, comprising:
a housing having a sensor portion at a distal end of the housing, and a handle portion between a proximal end and the distal end of the housing;
an ultrasound sensor positioned at least partially within the sensor portion of the housing; an electrocardiogram (EKG) sensor positioned at least partially within the sensor portion of the housing;
a first auscultation sensor and a second auscultation sensor;
an ambient noise sensor;
a first membrane adjacent to a first side of the ultrasound sensor, wherein the first auscultation sensor is positioned between the first membrane and the proximal end of the housing; and
a second membrane adjacent to a second side of the ultrasound sensor that is opposite the first side, wherein the second auscultation sensor is positioned between the second membrane and the proximal end of the housing; and
a processor communicatively coupled to the first and second auscultation sensors and the ambient noise sensor, the processor, in use, receives an auscultation signal sensed by the first and/or second auscultation sensor and an ambient noise signal sensed by the ambient noise sensor, and generates a noise-canceled auscultation signal in which the ambient noise signal is canceled from the auscultation signal.

12. The ultrasound probe of claim 11, wherein the first and second auscultation sensors are positioned at least partially within the sensor portion of the ultrasound probe, and the ambient noise sensor is positioned between the handle portion and the distal end of the ultrasound probe.

13. The ultrasound probe of claim 12 wherein the EKG sensor includes a first electrode adjacent to the first side of the ultrasound sensor, a second electrode adjacent to the second side of the ultrasound sensor that is opposite the first side, and a third electrode adjacent to a third side of the ultrasound sensor between the first and second sides of the ultrasound sensor.

14. The ultrasound probe of claim 13 wherein the first electrode of the EKG sensor extends through the first membrane, and the second electrode of the EKG sensor extends through the second membrane.

15. The ultrasound probe of claim 11 wherein the ambient noise sensor is mounted to the housing in a direction that is transverse to a direction in which the first and second auscultation sensors are oriented.

16. The ultrasound probe of claim 11 wherein the first auscultation sensor is spaced apart from the first membrane by a first gap, and the second auscultation sensor is spaced apart from the second membrane by a second gap.

17. The ultrasound probe of claim 16 wherein each of the first gap and the second gap is within a range of about 0.5 mm to about 1.5 mm, inclusive.

18. The ultrasound probe of claim 15 wherein the housing includes a third membrane over the ambient noise sensor.

* * * * *